United States Patent [19]
Badorf et al.

[11] Patent Number: 5,968,099
[45] Date of Patent: Oct. 19, 1999

[54] FIXATION OF A TIBIAL PART ON A TIBIAL PLATE OF A KNEE-JOINT ENDOPROSTHESIS

[75] Inventors: Dirk Badorf, Frechen; Hans-Georg Pfaff, Ostfildern, both of Germany

[73] Assignee: CeramTec AG Innovative Ceramic Engineering, Plochingen, Germany

[21] Appl. No.: 09/008,428

[22] Filed: Jan. 16, 1998

[30] Foreign Application Priority Data

Jan. 17, 1997 [DE] Germany ............................ 197 01 622
Mar. 1, 1997 [DE] Germany ............................ 197 08 375

[51] Int. Cl.⁶ ...................................................... A61F 2/38
[52] U.S. Cl. ................................................ 623/20; 606/88
[58] Field of Search .................................. 606/88, 89, 87, 606/86, 96; 623/20

[56] References Cited

U.S. PATENT DOCUMENTS 3,958,278  5/1976  Lee et al. .
4,944,757  7/1990  Martinez et al. .
5,358,527  10/1994  Forte .
5,470,354  11/1995  Hershberger et al. .................... 623/20
5,480,446  1/1996  Goodfellow .
5,514,183  5/1996  Epstein et al. ............................ 623/20
5,645,602  7/1997  Albrektsson et al. .................... 623/20

FOREIGN PATENT DOCUMENTS 0306744  3/1989  European Pat. Off. .
0672397  9/1995  European Pat. Off. .

*Primary Examiner*—Michael Buiz
*Assistant Examiner*—David O. Reip
*Attorney, Agent, or Firm*—Antonelli, Terry, Stout & Kraus, LLP

[57] ABSTRACT

The invention relates to a knee-joint endoprosthesis with a femoral part anchored in the femur and a tibial plate connected to the tibia bone, on which tibial plate tibial parts are arranged by way of gliding surfaces, and preferably with meniscus elements disposed between the femoral part and the tibial parts. With a view to mechanically stable anchorage of the tibial part on the tibial plate that may optionally be subsequently released, even at the implanted joint, so that the tibial part can be exchanged, it is proposed that the tibial part or parts are detachably connected to the tibial plate by wedging, screwing and/or bracing.

6 Claims, 2 Drawing Sheets

FIXATION OF A TIBIAL PART ON A TIBIAL PLATE OF A KNEE-JOINT ENDOPROSTHESIS

BACKGROUND OF THE INVENTION

A knee-joint endo-prosthesis is known from EP 0 442 330 B1 to have a femoral part, a meniscus element and a tibial part, the bearing surfaces of the femoral part and the tibial part bearing against associated bearing surfaces of the meniscus element.

The tibial part is firmly connected to a tibial plate, the tibial plate being anchored within the tibia bone and intended to knit together with the latter. The femoral part, tibial part and meniscus element are preferably produced from a ceramic material.

SUMMARY OF THE INVENTION

The object underlying the invention is to bring about a mechanically stable anchoring of the tibial part on the tibial plate that may optionally be subsequently released, even at the implanted joint, so that the tibial part can be exchanged.

In accordance with the invention this object is achieved by the tibial part or parts being detachably connected to the tibial plate by wedging, screwing and/or bracing.

Although the tibial parts are firmly anchored on the tibial plate by this means, the anchoring is optionally capable of being subsequently released, even at the implanted joint, as a result of which the tibial part or parts can be easily exchanged.

In a preferred embodiment a tensioning element that wedges and/or braces the tibial parts is attached to the tibial plate by means of a fixing screw. The tensioning element can be removed by loosening the fixing screw and the tibial parts can accordingly be withdrawn.

The tensioning element is preferably disposed between the tibial parts and simultaneously anchors both tibial parts on the tibial plate.

In advantageous manner the lateral surface of the tibial part facing the tensioning element and the adjoining lateral surface of the tensioning element here chamfers that match one another, the chamfer of the tensioning element resting against the chamfer of the tibial part. A stable anchorage is achieved in this way by clamping or anchoring.

In an advantageous configuration the tibial parts are inserted into an indentation in the tibial plate. This simplifies the anchorage, since the tibial parts are fixed horizontally by the edge of the indentation.

In advantageous manner at least one of the lateral surfaces of the indentation is provided with a notch that rests against the tibial part. To this end the tibial part has a bevel that is adapted to the notch and extends into the notch.

In a preferred embodiment the tibial parts consist of a ceramic material such as, for example, aluminium oxide, whereas the tibial plate consists, for example, of a titanium alloy.

BRIEF DESCRIPTION OF THE DRAWINGS

Further features of the invention will emerge from the following description with reference to the drawings, in which.

DETAILED DESCRIPTION OF THE PREFERRED EMBODIMENTS

Figure 1:
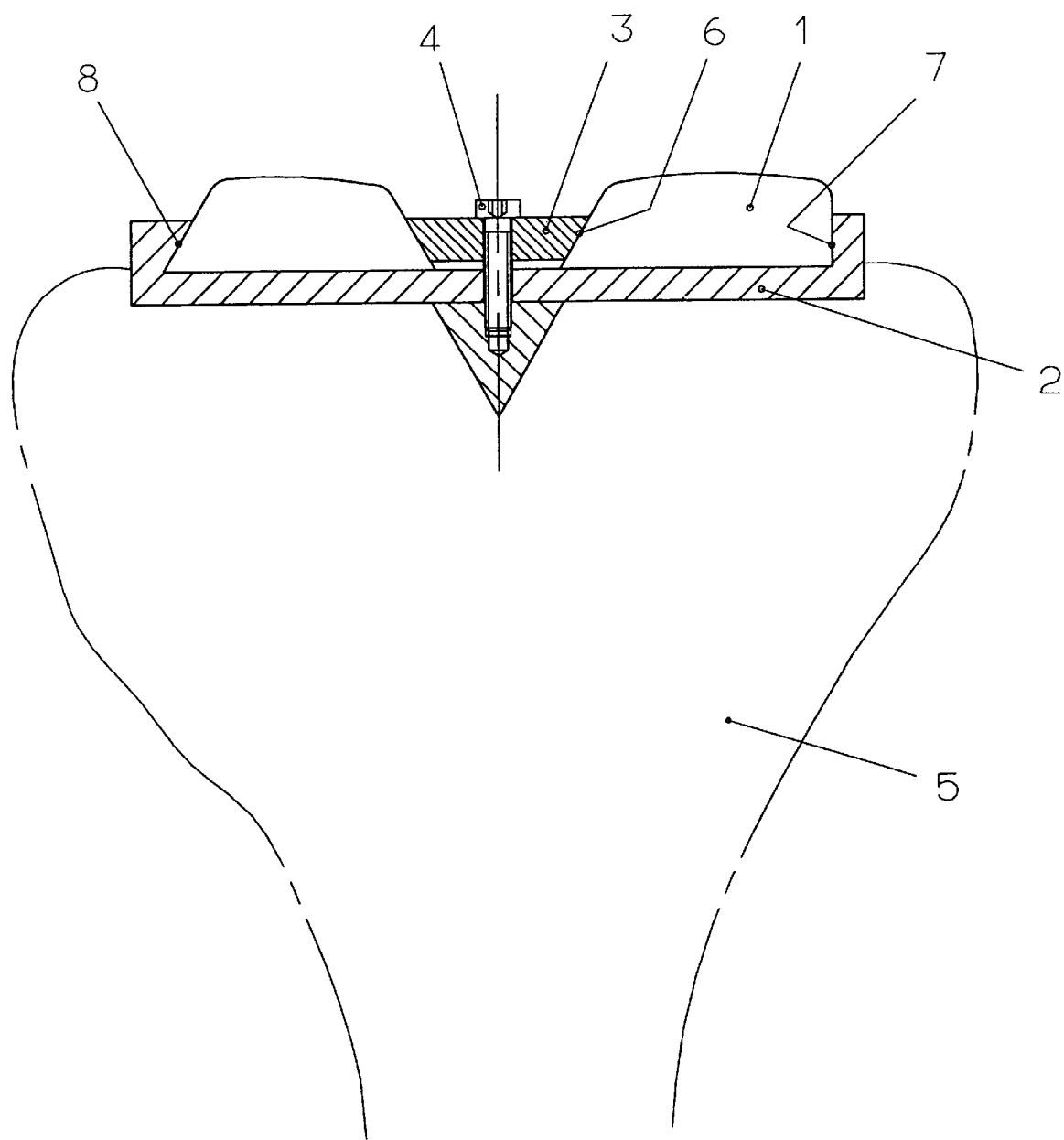
FIG. 1 is a sectional view of the knee-joint endoprosthesis of the present invention.

FIG. 1 shows a section through a tibia bone 5 with mounted tibial plate 2 and inserted tibial parts 1. Not shown is the remainder of the knee-joint endoprosthesis, namely the femoral part and the meniscus elements.

The tibial plate 2 is of plate-like design and has an indentation 7 on the side facing the femoral part. Into this indentation 7 are inserted two tibial parts 1 made of a ceramic material. These tibial parts 1 make contact with the lateral surfaces of the indentation 7 and are anchored by means of a centrally disposed tensioning element 3. The tensioning element 3 is attached to the tibial plate 2 by means of a fixing screw 4. The tensioning element 3 wedges and/or braces both tibial parts 1 simultaneously.

With a view to better anchorage, the lateral surfaces of the tibial part 1 and of the tensioning element 3 that are juxtaposed are provided with chamfers 6 that match one another, the chamfer of the tensioning element 3 resting against the chamfer of the tibial part 1.

With a view to additional anchorage, at least one of the lateral surfaces of the indentation 7 is provided with a notch 8, into which the adjoining lateral surface of the tibial part 1 projects, so that the lateral surface of the notch 8 rests against the bevel of the tibial part 1. This notch 8 is disposed in advantageous manner on all lateral surfaces of the tibial plate 2.

The tibial parts 1 consist of a ceramic material, whereas the tensioning element 3 and also the tibial plate 2 are produced from a titanium alloy.

By loosening the fixing screw 4 and removing the tensioning element 3, the tibial part 1 or the two tibial parts 1 can be easily withdrawn from the tibial plate 2 in the medial direction.

Figure 2:
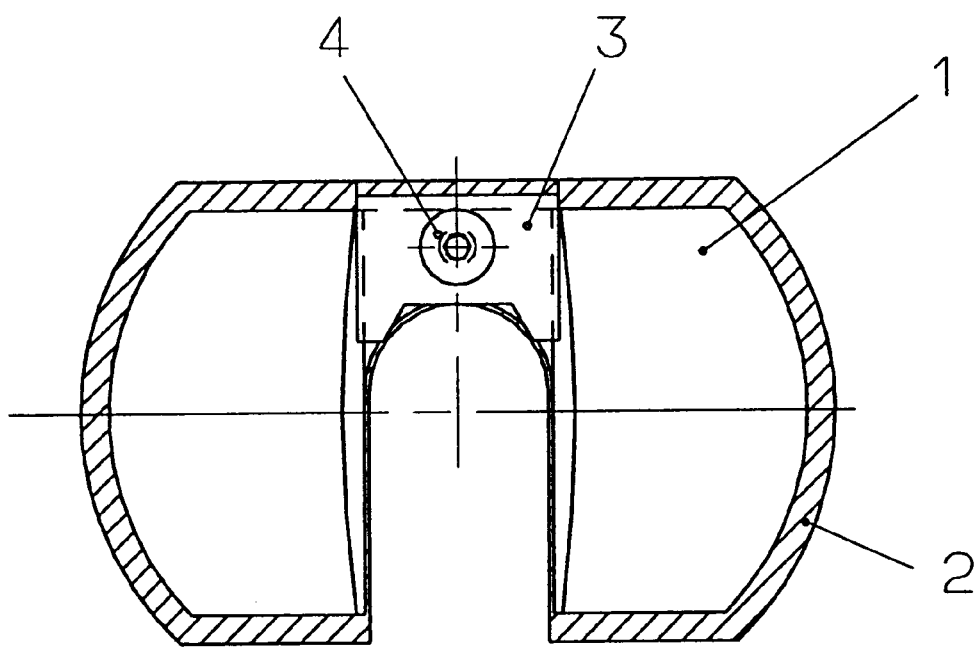
FIG. 2 is a top view of the tibial plate of the knee-joint prosthesis of the present invention.

FIG. 2 shows a top view of a tibial plate 2 with inserted tibial parts 2 according to FIG. 1 from the femoral side. The manner in which the tensioning element 3 rests against the chamfer 6 (see FIG. 1) of the tibial parts 1 and accordingly fixes the latter can be readily discerned.

The tibial parts 1 may also be screwed to the tibial plate 2 directly. To this end a bore in the tibial parts 1 is required, in which a screw is sunk. The attachment may be effected in all conceivable ways, but it has to be devised so as to be detachable.

I claim:

1. Knee-joint endoprosthesis comprising a femoral part anchorable in the femur; a tibial plate connectable to the tibia bone; tibial parts arranged by way of gliding surfaces on the tibial plate; and a tensioning element that wedges and/or braces the tibial parts, the tensioning element being attached to the tibial plate by a fixing screw.

2. Knee-joint endoprosthesis according to claim 1, wherein the tensioning element is disposed between the tibial parts and simultaneously anchors both tibial parts on the tibial plate.

3. Knee-joint endoprosthesis according to claim 1, wherein the lateral surface of the tibial part facing the tensioning element and an adjoining lateral surface of the tensioning element exhibit chamfers that match one another, the chamfer of the tensioning element resting against the chamfer of the tibial part.

4. Knee-joint endoprosthesis according to claim 1, wherein the tibial plate includes an indentation, and the tibial parts are inserted into the indentation in the tibial plate.

5. Knee-joint endoprosthesis according to claim 4, wherein at least one lateral surface of the indentation is provided with a notch that rests against one of the tibial parts.

6. Knee-joint endoprosthesis according to claim 1, wherein the tibial parts consist of a ceramic material.

* * * * *